(12) United States Patent
Greener

(10) Patent No.: US 11,357,903 B2
(45) Date of Patent: Jun. 14, 2022

(54) WOUND PACKING

(71) Applicant: Smith & Nephew PLC, Watford (GB)

(72) Inventor: Bryan Greener, York (GB)

(73) Assignee: Smith & Nephew PLC, Watford (GB)

( * ) Notice: Subject to any disclaimer, the term of this patent is extended or adjusted under 35 U.S.C. 154(b) by 407 days.

(21) Appl. No.: 16/524,484

(22) Filed: Jul. 29, 2019

(65) Prior Publication Data

US 2019/0343994 A1   Nov. 14, 2019

Related U.S. Application Data

(63) Continuation of application No. 15/187,558, filed on Jun. 20, 2016, now Pat. No. 10,363,345, which is a
(Continued)

(30) Foreign Application Priority Data

Feb. 13, 2009 (GB) ...................................... 0902368

(51) Int. Cl.
*A61F 13/00* (2006.01)
*A61M 1/00* (2006.01)
(Continued)

(52) U.S. Cl.
CPC ......... *A61M 1/90* (2021.05); *A61F 13/00068* (2013.01); *A61F 13/00987* (2013.01); *A61F 13/0276* (2013.01); *A61F 15/001* (2013.01); *A61L 15/425* (2013.01); *A61F 2013/00357* (2013.01); *Y10T 29/49826* (2015.01); *Y10T 83/0341* (2015.04); *Y10T 83/04* (2015.04); *Y10T 83/0524* (2015.04)

(58) Field of Classification Search
None
See application file for complete search history.

(56) References Cited

U.S. PATENT DOCUMENTS

| | | |
|---|---|---|
| 1,066,934 A | 7/1913 | Manney |
| 1,975,504 A | 10/1934 | Formhals |
| | (Continued) | |

FOREIGN PATENT DOCUMENTS

| | | |
|---|---|---|
| CN | 1293953 A | 5/2001 |
| CN | 2676918 Y | 2/2005 |
| | (Continued) | |

OTHER PUBLICATIONS

Thomas, S. et al., "Hydrocolloids: A guide to composition, properties and uses of hydrocolloid dressings and the commercial presentations available," J. of Wound Care, vol. 1, No. 2, Jul.-Aug. 1992, pp. 27-30, in 5 pages.
(Continued)

*Primary Examiner* — Kim M Lewis
(74) *Attorney, Agent, or Firm* — Knobbe, Martens, Olson & Bear, LLP

(57) ABSTRACT

A wound packing material is provided, suitable for use in negative pressure wound therapy, including a body of a porous material, the body including frangible regions defining a plurality of portions, the frangible regions allowing the portions to be selectively removed from the body. Methods of manufacturing the wound packing material, and methods of its use are also provided.

17 Claims, 4 Drawing Sheets

Related U.S. Application Data continuation of application No. 14/328,323, filed on Jul. 10, 2014, now Pat. No. 9,370,450, which is a continuation of application No. 13/201,427, filed as application No. PCT/GB2010/000228 on Feb. 10, 2010, now Pat. No. 8,791,316.

(51) Int. Cl.
*A61F 13/02* (2006.01)
*A61F 15/00* (2006.01)
*A61L 15/42* (2006.01)

(56) References Cited

U.S. PATENT DOCUMENTS

| | | |
|---|---|---|
| 2,331,271 A | 10/1943 | Gilchrist |
| 2,727,382 A | 12/1955 | Kurz |
| 2,877,765 A | 3/1959 | Bunyan |
| 2,889,039 A | 6/1959 | Schladermundt et al. |
| 3,073,304 A | 1/1963 | Schaar |
| 3,285,245 A | 11/1966 | Eldredge et al. |
| 3,964,039 A | 6/1976 | Craford et al. |
| 4,093,277 A | 6/1978 | Nolan et al. |
| 4,095,599 A | 6/1978 | Simonet-Haibe |
| 4,224,941 A | 9/1980 | Stivala |
| 4,252,119 A | 2/1981 | Coates |
| 4,294,240 A | 10/1981 | Thill |
| 4,341,207 A | 7/1982 | Steer et al. |
| 4,360,015 A | 11/1982 | Mayer |
| 4,360,021 A | 11/1982 | Stima |
| 4,418,691 A | 12/1983 | Yannas et al. |
| 4,499,896 A | 2/1985 | Heinecke |
| 4,541,426 A | 9/1985 | Webster |
| 4,561,435 A | 12/1985 | McKnight et al. |
| 4,624,656 A | 11/1986 | Clark et al. |
| 4,664,662 A | 5/1987 | Webster |
| 4,681,562 A | 7/1987 | Beck et al. |
| 4,690,134 A | 9/1987 | Snyders |
| 4,699,134 A | 10/1987 | Samuelsen |
| 4,735,606 A | 4/1988 | Davison |
| 4,759,354 A | 7/1988 | Quarfoot |
| 4,770,187 A | 9/1988 | Lash et al. |
| 4,798,603 A | 1/1989 | Meyer et al. |
| 4,867,150 A | 9/1989 | Gilbert |
| 4,875,473 A | 10/1989 | Alvarez |
| 4,882,213 A | 11/1989 | Gaddis et al. |
| 4,886,697 A | 12/1989 | Perdelwitz, Jr. et al. |
| 4,929,477 A | 5/1990 | Will |
| 4,969,880 A | 11/1990 | Zamierowski |
| 4,985,467 A | 1/1991 | Kelly et al. |
| 4,997,425 A | 3/1991 | Shioya et al. |
| 5,000,172 A | 3/1991 | Ward |
| 5,000,741 A | 3/1991 | Kalt |
| 5,080,661 A | 1/1992 | Lavender et al. |
| 5,149,331 A | 9/1992 | Ferdman et al. |
| 5,152,757 A | 10/1992 | Eriksson |
| 5,167,613 A | 12/1992 | Karami et al. |
| 5,218,973 A | 6/1993 | Weaver et al. |
| 5,261,893 A | 11/1993 | Zamierowski |
| 5,264,218 A | 11/1993 | Rogozinski |
| 5,267,952 A | 12/1993 | Gardner |
| 5,322,695 A | 6/1994 | Shah et al. |
| 5,336,209 A | 8/1994 | Porzilli |
| 5,360,420 A | 11/1994 | Cook et al. |
| 5,397,316 A | 3/1995 | LaVon et al. |
| 5,415,715 A | 5/1995 | Delage et al. |
| 5,445,604 A | 8/1995 | Lang |
| 5,486,158 A | 1/1996 | Samuelson |
| 5,489,304 A | 2/1996 | Orgill et al. |
| 5,496,605 A | 3/1996 | Augst et al. |
| 5,527,293 A | 6/1996 | Zamierowski |
| 5,536,555 A | 7/1996 | Zelazoski et al. |
| 5,549,584 A | 8/1996 | Gross |
| 5,562,107 A | 10/1996 | Lavender et al. |
| 5,591,149 A | 1/1997 | Cree et al. |
| 5,593,395 A | 1/1997 | Martz |
| 5,599,289 A | 2/1997 | Castellana |
| 5,616,387 A | 4/1997 | Augst et al. |
| 5,626,954 A | 5/1997 | Anderson |
| 5,633,007 A | 5/1997 | Webb et al. |
| 5,636,643 A | 6/1997 | Argenta et al. |
| 5,643,189 A | 7/1997 | Masini |
| 5,645,081 A | 7/1997 | Argenta et al. |
| 5,681,579 A | 10/1997 | Freeman |
| 5,713,881 A | 2/1998 | Rezai et al. |
| 5,714,225 A | 2/1998 | Hansen et al. |
| 5,716,411 A | 2/1998 | Orgill et al. |
| 5,720,714 A | 2/1998 | Penrose |
| 5,733,305 A | 3/1998 | Fleischmann |
| 5,759,570 A | 6/1998 | Arnold |
| 5,792,090 A | 8/1998 | Ladin |
| 5,795,439 A | 8/1998 | Euripides et al. |
| 5,795,584 A | 8/1998 | Totakura et al. |
| 5,804,021 A | 9/1998 | Abuto et al. |
| 5,810,755 A | 9/1998 | LeVeen et al. |
| 5,833,646 A | 11/1998 | Masini |
| D403,774 S | 1/1999 | Laughlin et al. |
| 5,868,724 A | 2/1999 | Dierckes, Jr. et al. |
| 5,885,237 A | 3/1999 | Kadash et al. |
| D408,920 S | 4/1999 | Dunshee et al. |
| 5,899,893 A | 5/1999 | Dyer et al. |
| 5,958,420 A | 9/1999 | Jenson |
| D415,836 S | 10/1999 | Dunshee et al. |
| 5,968,855 A | 10/1999 | Perdelwitz, Jr. et al. |
| 5,981,822 A | 11/1999 | Addison |
| 5,985,990 A | 11/1999 | Kantner et al. |
| 6,018,092 A | 1/2000 | Dunshee |
| 6,071,267 A | 6/2000 | Zamierowski |
| 6,087,549 A | 7/2000 | Flick |
| 6,117,111 A | 9/2000 | Fleischmann |
| 6,142,982 A | 11/2000 | Hunt et al. |
| 6,167,613 B1 | 1/2001 | Karami |
| 6,203,563 B1 | 3/2001 | Fernandez |
| 6,203,654 B1 | 3/2001 | McFall et al. |
| 6,207,875 B1 | 3/2001 | Lindqvist et al. |
| 6,225,523 B1 | 5/2001 | Masini |
| 6,261,283 B1 | 7/2001 | Morgan et al. |
| 6,293,281 B1 | 9/2001 | Shultz et al. |
| 6,297,422 B1 | 10/2001 | Hansen et al. |
| 6,333,093 B1 | 12/2001 | Burrell et al. |
| 6,345,623 B1 | 2/2002 | Heaton et al. |
| 6,350,339 B1 | 2/2002 | Sessions |
| 6,398,767 B1 | 6/2002 | Fleischmann |
| 6,447,799 B1 | 9/2002 | Ullman |
| 6,458,109 B1 | 10/2002 | Henley et al. |
| 6,478,781 B1 | 11/2002 | Urich et al. |
| 6,482,491 B1 | 11/2002 | Samuelsen et al. |
| 6,497,688 B2 | 12/2002 | Lasko |
| 6,553,998 B2 | 4/2003 | Heaton et al. |
| 6,566,575 B1 | 5/2003 | Stickels et al. |
| 6,599,262 B1 | 7/2003 | Masini |
| 6,680,113 B1 | 1/2004 | Lucast et al. |
| 6,685,681 B2 | 2/2004 | Lockwood et al. |
| 6,713,659 B2 | 3/2004 | Bodenschatz et al. |
| 6,752,794 B2 | 6/2004 | Lockwood et al. |
| 6,767,334 B1 | 7/2004 | Randolph |
| 6,770,794 B2 | 8/2004 | Fleischmann |
| 6,794,554 B2 | 9/2004 | Sessions et al. |
| 6,797,855 B2 | 9/2004 | Worthley |
| 6,814,079 B2 | 11/2004 | Heaton et al. |
| 6,838,589 B2 | 1/2005 | Liedtke et al. |
| 6,855,135 B2 | 2/2005 | Lockwood et al. |
| D506,547 S | 6/2005 | Cruz et al. |
| 6,942,628 B1 | 9/2005 | Watson |
| 6,951,553 B2 | 10/2005 | Bubb et al. |
| 6,974,428 B2 | 12/2005 | Knutson et al. |
| 6,979,324 B2 | 12/2005 | Bybordi et al. |
| 6,998,511 B2 | 2/2006 | Worthley |
| 7,004,915 B2 | 2/2006 | Boynton et al. |
| 7,005,556 B1 | 2/2006 | Becker et al. |
| 7,022,113 B2 | 4/2006 | Lockwood et al. |
| 7,030,288 B2 | 4/2006 | Liedtke et al. |
| 7,041,868 B2 | 5/2006 | Greene et al. |
| 7,070,584 B2 | 7/2006 | Johnson et al. |

(56) References Cited

U.S. PATENT DOCUMENTS

| | | |
|---|---|---|
| 7,108,681 B2 | 9/2006 | Gartstein et al. |
| 7,108,683 B2 | 9/2006 | Zamierowski |
| 7,122,712 B2 | 10/2006 | Lutri et al. |
| 7,137,968 B1 | 11/2006 | Burrell et al. |
| D537,948 S | 3/2007 | Smith |
| D544,607 S | 6/2007 | Henry et al. |
| 7,267,681 B2 | 9/2007 | Dunshee |
| 7,291,762 B2 | 11/2007 | Flick |
| 7,335,809 B2 | 2/2008 | Riesinger |
| 7,338,482 B2 | 3/2008 | Lockwood et al. |
| 7,351,250 B2 | 4/2008 | Zamierowski |
| 7,381,859 B2 | 6/2008 | Hunt et al. |
| 7,429,689 B2 | 9/2008 | Chen et al. |
| 7,438,705 B2 | 10/2008 | Karpowicz et al. |
| 7,468,471 B2 | 12/2008 | Sigurjonsson et al. |
| 7,494,482 B2 | 2/2009 | Orgill et al. |
| 7,518,031 B2 | 4/2009 | Liedtke et al. |
| 7,534,927 B2 | 5/2009 | Lockwood et al. |
| 7,553,306 B1 | 6/2009 | Hunt et al. |
| 7,576,256 B2 | 8/2009 | Bjornberg et al. |
| 7,615,036 B2 | 11/2009 | Joshi et al. |
| 7,625,362 B2 | 12/2009 | Boehringer et al. |
| 7,645,269 B2 | 1/2010 | Zamierowski |
| 7,676,400 B1 | 3/2010 | Dillon |
| 7,676,784 B2 | 3/2010 | Allen et al. |
| 7,678,102 B1 | 3/2010 | Heaton |
| 7,700,819 B2 | 4/2010 | Ambrosio et al. |
| 7,722,582 B2 | 5/2010 | Lina et al. |
| D620,122 S | 7/2010 | Cotton |
| D620,123 S | 7/2010 | Igwebuike |
| 7,753,894 B2 | 7/2010 | Blott et al. |
| 7,754,937 B2 | 7/2010 | Boehringer et al. |
| 7,759,537 B2 | 7/2010 | Bishop et al. |
| 7,779,625 B2 | 8/2010 | Joshi et al. |
| 7,790,946 B2 | 9/2010 | Mulligan |
| 7,794,438 B2 | 9/2010 | Henley et al. |
| 7,812,212 B2 | 10/2010 | Propp et al. |
| 7,815,616 B2 | 10/2010 | Boehringer et al. |
| 7,820,453 B2 | 10/2010 | Heylen et al. |
| 7,846,141 B2 | 12/2010 | Weston |
| 7,857,806 B2 | 12/2010 | Karpowicz et al. |
| 7,896,856 B2 | 3/2011 | Petrosenko et al. |
| 7,909,805 B2 | 3/2011 | Weston |
| 7,942,866 B2 | 5/2011 | Radi et al. |
| 7,951,100 B2 | 5/2011 | Hunt et al. |
| D639,441 S | 6/2011 | Sferle |
| 7,976,519 B2 | 7/2011 | Bubb et al. |
| 7,981,098 B2 | 7/2011 | Boehringer et al. |
| 7,982,087 B2 | 7/2011 | Greener et al. |
| D644,330 S | 8/2011 | Pfeiffer et al. |
| 8,030,534 B2 | 10/2011 | Radi et al. |
| 8,034,037 B2 | 10/2011 | Adams et al. |
| 8,062,272 B2 | 11/2011 | Weston |
| 8,062,331 B2 | 11/2011 | Zamierowski |
| 8,070,773 B2 | 12/2011 | Zamierowski |
| 8,097,272 B2 | 1/2012 | Addison |
| RE43,195 E | 2/2012 | Cotton |
| 8,114,126 B2 | 2/2012 | Heaton et al. |
| 8,123,781 B2 | 2/2012 | Zamierowski |
| 8,142,419 B2 | 3/2012 | Heaton et al. |
| 8,172,816 B2 | 5/2012 | Kazala, Jr. et al. |
| 8,187,237 B2 | 5/2012 | Seegert |
| 8,188,331 B2 | 5/2012 | Barta et al. |
| 8,192,409 B2 | 6/2012 | Hardman et al. |
| 8,197,467 B2 | 6/2012 | Heaton et al. |
| 8,273,105 B2 | 9/2012 | Cohen et al. |
| 8,338,402 B2 | 12/2012 | Fry et al. |
| 8,353,931 B2 | 1/2013 | Stopek et al. |
| 8,372,050 B2 | 2/2013 | Jaeb et al. |
| 8,376,972 B2 | 2/2013 | Fleischmann |
| 8,399,730 B2 | 3/2013 | Kazala, Jr. et al. |
| 8,444,392 B2 | 5/2013 | Turner et al. |
| 8,447,375 B2 | 5/2013 | Shuler |
| 8,460,257 B2 | 6/2013 | Locke et al. |
| 8,486,032 B2 | 7/2013 | Seegert et al. |
| 8,500,704 B2 | 8/2013 | Boehringer et al. |
| 8,500,776 B2 | 8/2013 | Ebner |
| 8,523,832 B2 | 9/2013 | Seegert |
| 8,535,296 B2 | 9/2013 | Blott et al. |
| 8,540,687 B2 | 9/2013 | Henley et al. |
| D692,565 S | 10/2013 | Lattimore et al. |
| 8,608,776 B2 | 12/2013 | Coward et al. |
| 8,622,981 B2 | 1/2014 | Hartwell et al. |
| 8,632,523 B2 | 1/2014 | Eriksson et al. |
| 8,679,080 B2 | 3/2014 | Kazala, Jr. et al. |
| 8,680,360 B2 | 3/2014 | Greener et al. |
| 8,764,732 B2 | 7/2014 | Hartwell |
| 8,791,315 B2 | 7/2014 | Lattimore et al. |
| 8,791,316 B2 | 7/2014 | Greener |
| 8,801,685 B2 | 8/2014 | Armstrong et al. |
| 8,821,535 B2 | 9/2014 | Greener |
| 8,843,327 B2 | 9/2014 | Vernon-Harcourt et al. |
| 8,945,030 B2 | 2/2015 | Weston |
| 9,220,822 B2 | 12/2015 | Hartwell et al. |
| 10,363,345 B2 | 7/2019 | Greener |
| 2001/0027285 A1 | 10/2001 | Heinecke et al. |
| 2001/0034499 A1 | 10/2001 | Sessions et al. |
| 2001/0051165 A1 | 12/2001 | Lenz et al. |
| 2002/0035352 A1 | 3/2002 | Ronnberg et al. |
| 2002/0052570 A1 | 5/2002 | Naimer |
| 2002/0082567 A1 | 6/2002 | Lockwood et al. |
| 2002/0161346 A1 | 10/2002 | Lockwood et al. |
| 2002/0183702 A1 | 12/2002 | Henley et al. |
| 2002/0193721 A1 | 12/2002 | Vandruff |
| 2003/0014025 A1 | 1/2003 | Allen et al. |
| 2003/0014786 P1 | 1/2003 | Meilland |
| 2003/0050590 A1 | 3/2003 | Kirsch |
| 2003/0212357 A1 | 11/2003 | Pace |
| 2004/0006319 A1 | 1/2004 | Lina et al. |
| 2004/0019337 A1 | 1/2004 | Moberg-Alehammar et al. |
| 2004/0019338 A1 | 1/2004 | Litvay et al. |
| 2004/0064111 A1 | 4/2004 | Lockwood et al. |
| 2004/0087884 A1 | 5/2004 | Haddock et al. |
| 2004/0167482 A1 | 8/2004 | Watson |
| 2005/0084641 A1 | 4/2005 | Downs et al. |
| 2005/0085795 A1 | 4/2005 | Lockwood |
| 2005/0090860 A1 | 4/2005 | Paprocki |
| 2005/0113733 A1 | 5/2005 | Liedtke et al. |
| 2005/0131327 A1 | 6/2005 | Lockwood et al. |
| 2005/0143697 A1 | 6/2005 | Riesinger |
| 2005/0181163 A1 | 8/2005 | Kose |
| 2005/0182445 A1 | 8/2005 | Zamierowski |
| 2005/0197626 A1 | 9/2005 | Moberg et al. |
| 2005/0215932 A1 | 9/2005 | Sigurjonsson et al. |
| 2005/0267424 A1 | 12/2005 | Eriksson et al. |
| 2006/0020234 A1 | 1/2006 | Chou et al. |
| 2006/0047257 A1 | 3/2006 | Raidel et al. |
| 2006/0142687 A1 | 6/2006 | Liedtke et al. |
| 2006/0161123 A1 | 7/2006 | Kudo et al. |
| 2006/0178608 A1 | 8/2006 | Stapf |
| 2006/0184150 A1 | 8/2006 | Noel |
| 2006/0241689 A1 | 10/2006 | Leiboff et al. |
| 2007/0010775 A1 | 1/2007 | Lutri |
| 2007/0032763 A1 | 2/2007 | Vogel |
| 2007/0060892 A1 | 3/2007 | Propp |
| 2007/0073200 A1 | 3/2007 | Hannigan et al. |
| 2007/0142761 A1 | 6/2007 | Aali |
| 2007/0185463 A1 | 8/2007 | Mulligan |
| 2007/0220692 A1 | 9/2007 | Kusin |
| 2007/0239232 A1 | 10/2007 | Kurtz et al. |
| 2007/0282309 A1 | 12/2007 | Bengtson et al. |
| 2008/0095979 A1 | 4/2008 | Hatanaka et al. |
| 2008/0172017 A1 | 7/2008 | Carlucci et al. |
| 2008/0213344 A1 | 9/2008 | McCarthy et al. |
| 2008/0300555 A1 | 12/2008 | Olson et al. |
| 2009/0005744 A1 | 1/2009 | Karpowicz et al. |
| 2009/0012483 A1 | 1/2009 | Blott et al. |
| 2009/0043268 A1 | 2/2009 | Eddy et al. |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0105671 A1 | 4/2009 | Daggar et al. |
| 2009/0130186 A1 | 5/2009 | McCarthy et al. |
| 2009/0137973 A1 | 5/2009 | Karpowicz et al. |

(56) References Cited

U.S. PATENT DOCUMENTS

| | | |
|---|---|---|
| 2009/0177136 A1 | 7/2009 | Liedtke et al. |
| 2009/0227968 A1 | 9/2009 | Vess |
| 2009/0227969 A1 | 9/2009 | Jaeb et al. |
| 2009/0234309 A1 | 9/2009 | Vitaris et al. |
| 2009/0299255 A1 | 12/2009 | Kazala, Jr. et al. |
| 2009/0306609 A1 | 12/2009 | Blott et al. |
| 2009/0326430 A1 | 12/2009 | Frederiksen et al. |
| 2010/0010462 A1 | 1/2010 | Kurata |
| 2010/0022990 A1 | 1/2010 | Karpowicz et al. |
| 2010/0063484 A1 | 3/2010 | Heagle |
| 2010/0069829 A1 | 3/2010 | Hutchinson et al. |
| 2010/0069858 A1 | 3/2010 | Olson |
| 2010/0069885 A1 | 3/2010 | Stevenson et al. |
| 2010/0087767 A1 | 4/2010 | McNeil |
| 2010/0106113 A1 | 4/2010 | Heinecke |
| 2010/0106117 A1 | 4/2010 | Lockwood et al. |
| 2010/0106184 A1 | 4/2010 | Coward et al. |
| 2010/0125234 A1 | 5/2010 | Smith |
| 2010/0125258 A1 | 5/2010 | Coulthard et al. |
| 2010/0137775 A1 | 6/2010 | Hu et al. |
| 2010/0160874 A1 | 6/2010 | Robinson et al. |
| 2010/0160876 A1 | 6/2010 | Robinson et al. |
| 2010/0174250 A1 | 7/2010 | Hu et al. |
| 2010/0179463 A1 | 7/2010 | Greener et al. |
| 2010/0179515 A1 | 7/2010 | Swain et al. |
| 2010/0196106 A1 | 8/2010 | Allen |
| 2010/0249733 A9 | 9/2010 | Blott et al. |
| 2010/0305526 A1 | 12/2010 | Robinson et al. |
| 2010/0312159 A1 | 12/2010 | Aali et al. |
| 2011/0004172 A1 | 1/2011 | Eckstein et al. |
| 2011/0021964 A1 | 1/2011 | Larsen et al. |
| 2011/0034892 A1 | 2/2011 | Buan |
| 2011/0054283 A1 | 3/2011 | Shuler |
| 2011/0066096 A1 | 3/2011 | Svedman |
| 2011/0070391 A1 | 3/2011 | Cotton |
| 2011/0077605 A1 | 3/2011 | Karpowicz et al. |
| 2011/0112492 A1 | 5/2011 | Bharti et al. |
| 2011/0178451 A1 | 7/2011 | Robinson et al. |
| 2011/0184364 A1 | 7/2011 | Biggs et al. |
| 2011/0282310 A1 | 11/2011 | Boehringer et al. |
| 2011/0319801 A1 | 12/2011 | Ital et al. |
| 2012/0041402 A1 | 2/2012 | Greener |
| 2012/0059412 A1 | 3/2012 | Fleischmann |
| 2012/0095380 A1 | 4/2012 | Gergely et al. |
| 2012/0130326 A1 | 5/2012 | Cavanaugh, II et al. |
| 2012/0136328 A1 | 5/2012 | Johannison et al. |
| 2012/0144989 A1 | 6/2012 | De Plessis et al. |
| 2012/0150133 A1 | 6/2012 | Heaton et al. |
| 2012/0172926 A1 | 7/2012 | Hotter |
| 2012/0191054 A1 | 7/2012 | Kazala, Jr. et al. |
| 2012/0308780 A1 | 12/2012 | Rottger et al. |
| 2013/0197457 A1 | 8/2013 | Kazala et al. |
| 2013/0211349 A1 | 8/2013 | Stokes et al. |
| 2013/0253401 A1 | 9/2013 | Locke et al. |
| 2014/0068914 A1 | 3/2014 | Coward et al. |
| 2014/0094730 A1 | 4/2014 | Greener |
| 2014/0323998 A1 | 10/2014 | Greener |

FOREIGN PATENT DOCUMENTS

| | | | | |
|---|---|---|---|---|
| CN | 2843399 Y | 12/2006 | | |
| CN | 201139694 Y | 10/2008 | | |
| CN | 101415818 A | 4/2009 | | |
| CN | 201375590 Y | 1/2010 | | |
| CN | 201418816 Y | 3/2010 | | |
| CN | 102089017 A | 6/2011 | | |
| CN | 102458334 A | 5/2012 | | |
| DE | 3 539 533 | 5/1987 | | |
| DE | 4030465 A1 | 4/1992 | | |
| DE | 10 2005 007016 | 8/2006 | | |
| EP | 0 122 085 | 6/1987 | | |
| EP | 0 418 607 | 3/1991 | | |
| EP | 0 485 657 | 5/1992 | | |
| EP | 0 617 938 | 10/1994 | | |
| EP | 0 638 301 | 2/1995 | | |
| EP | 0 465 601 | 1/1997 | | |
| EP | 0 762 860 | 3/1997 | | |
| EP | 0768071 A1 | 4/1997 | | |
| EP | 0 853 950 | 7/1998 | | |
| EP | 0 651 983 | 9/1998 | | |
| EP | 0 777 504 | 10/1998 | | |
| EP | 0 688 189 | 9/2000 | | |
| EP | 0 670 705 | 5/2001 | | |
| EP | 1 320 342 | 6/2003 | | |
| EP | 1 088 569 | 8/2003 | | |
| EP | 1353001 A1 | 10/2003 | | |
| EP | 1 219311 | 7/2004 | | |
| EP | 1 018 967 | 8/2004 | | |
| EP | 0630629 B1 | 11/2004 | | |
| EP | 1 614 789 | 1/2006 | | |
| EP | 1620720 A1 | 2/2006 | | |
| EP | 1 440 667 | 3/2006 | | |
| EP | 1 284 777 | 4/2006 | | |
| EP | 0 620 720 | 11/2006 | | |
| EP | 1 772 160 | 4/2007 | | |
| EP | 2 214 728 | 8/2010 | | |
| EP | 2 279 016 | 2/2011 | | |
| EP | 2 366 721 | 9/2011 | | |
| EP | 2 341 955 | 12/2012 | | |
| EP | 2 567 717 | 3/2013 | | |
| EP | 2 594 299 | 5/2013 | | |
| EP | 2 601 984 | 6/2013 | | |
| EP | 2 623 137 | 8/2013 | | |
| EP | 2269603 B1 | 5/2015 | | |
| FR | 1 163 907 | 10/1958 | | |
| FR | 1163907 A | * 10/1958 | ............ | A61B 17/50 |
| GB | 821959 | 10/1959 | | |
| GB | 1063066 | 3/1967 | | |
| GB | 1224009 | 3/1971 | | |
| GB | 2085305 | 1/1985 | | |
| GB | 2195255 | 4/1988 | | |
| GB | 2329127 | 3/1999 | | |
| GB | 2331937 A | 6/1999 | | |
| GB | 2305610 | 7/1999 | | |
| GB | 2357286 | 11/2003 | | |
| GB | 2389794 | 12/2003 | | |
| GB | 2365350 | 8/2004 | | |
| GB | 2423019 | 8/2006 | | |
| JP | S5230463 U | 3/1977 | | |
| JP | S57119738 A | 7/1982 | | |
| JP | H02-139624 | 11/1990 | | |
| JP | H02-139625 | 11/1990 | | |
| JP | H02131432 U | 11/1990 | | |
| JP | H06-339495 | 12/1994 | | |
| JP | H0788131 A | 4/1995 | | |
| JP | H07231909 A | 9/1995 | | |
| JP | H11-056900 | 3/1999 | | |
| JP | 2004-000465 | 1/2004 | | |
| JP | 2006025918 A | 2/2006 | | |
| JP | 2008073187 A | 4/2008 | | |
| JP | 2008183244 A | 8/2008 | | |
| JP | 2011521736 A | 7/2011 | | |
| JP | 2011530344 A | 12/2011 | | |
| RU | 62504 U1 | 4/2007 | | |
| WO | WO 1990/010424 | 9/1990 | | |
| WO | WO 1992/010983 | 7/1992 | | |
| WO | WO 1992/013713 | 8/1992 | | |
| WO | WO 1993/000056 | 1/1993 | | |
| WO | WO 1994/020041 | 9/1994 | | |
| WO | WO 1995/014451 | 6/1995 | | |
| WO | WO 1996/001731 | 1/1996 | | |
| WO | WO 1996/024316 | 8/1996 | | |
| WO | WO 1997/11658 | 4/1997 | | |
| WO | WO 1997/043991 | 11/1997 | | |
| WO | WO-9741816 A1 | 11/1997 | | |
| WO | WO 1998/038955 | 9/1998 | | |
| WO | WO-9963922 A1 | 12/1999 | | |
| WO | WO 2000/007653 | 2/2000 | | |
| WO | WO 2000/061206 | 10/2000 | | |
| WO | WO 2001/049233 | 7/2001 | | |
| WO | WO-0154743 A1 | 8/2001 | | |
| WO | WO 2002/005737 | 1/2002 | | |
| WO | WO 2002/26180 | 4/2002 | | |
| WO | WO 2002/039940 | 5/2002 | | |

(56) References Cited

FOREIGN PATENT DOCUMENTS

| WO | WO 2002/041878 | 5/2002 |
|---|---|---|
| WO | WO 2002/045761 | 6/2002 |
| WO | WO 2002/091965 | 11/2002 |
| WO | WO 2002/092783 | 11/2002 |
| WO | WO 2003/051409 | 6/2003 |
| WO | WO 2003/072748 | 9/2003 |
| WO | WO 2003/086232 | 10/2003 |
| WO | WO 2004/018020 | 3/2004 |
| WO | WO 2005/009488 | 2/2005 |
| WO | WO 2006/099137 | 9/2006 |
| WO | WO 2006/130594 | 12/2006 |
| WO | WO-2007066699 A1 | 6/2007 |
| WO | WO 2007/075379 | 7/2007 |
| WO | WO 2008/039839 | 4/2008 |
| WO | WO 2008/040681 | 4/2008 |
| WO | WO 2008/064502 | 6/2008 |
| WO | WO 2008/064503 | 6/2008 |
| WO | WO-2008100437 A1 | 8/2008 |
| WO | WO 2008/104609 | 9/2008 |
| WO | WO 2008/141228 | 11/2008 |
| WO | WO-2009001590 A1 | 12/2008 |
| WO | WO 2009/011856 | 1/2009 |
| WO | WO 2009/021523 | 2/2009 |
| WO | WO 2009/070905 | 6/2009 |
| WO | WO 2009/112848 | 9/2009 |
| WO | WO-2009114760 A1 | 9/2009 |
| WO | WO-2009135171 A2 | 11/2009 |
| WO | WO-2009156949 A2 | 12/2009 |
| WO | WO-2009158131 A1 | 12/2009 |
| WO | WO 2010/010398 | 1/2010 |
| WO | WO 2010/016791 | 2/2010 |
| WO | WO 2010/033271 | 3/2010 |
| WO | WO 2010/033574 | 3/2010 |
| WO | WO 2010/033613 | 3/2010 |
| WO | WO 2010/051068 | 5/2010 |
| WO | WO 2010/072309 | 7/2010 |
| WO | WO 2010/075178 | 7/2010 |
| WO | WO 2010/097570 | 9/2010 |
| WO | WO-2010122665 A1 | 10/2010 |
| WO | WO-2011028407 A1 | 3/2011 |
| WO | WO-2011087871 A2 | 7/2011 |
| WO | WO 2011/106722 | 9/2011 |
| WO | WO 2012/138514 | 10/2012 |

OTHER PUBLICATIONS

Alexander, J. et al., "Clinical Evaluation of Epigard, a New Synthetic Substitute for Homograft and Heterograft Skin", The Journal of Trauma, vol. 13, No. 4, Apr. 1973, pp. 374-383, in 10 pages.

Applications for Modification to HCPCS Level II Code Set in the 2005-2006 Coding Cycle, in 60 pages. URL: www.cms.hhs.gov/medicare/hcpcs/.

Bagautdinov, N.A., "Variant of External Vacuum Aspiration in the Treatment of Purulent Diseases of Soft Tissues", in Current Problems in Modern Clinical Surgery: Interdepartmental Collection, edited by V. Ye. Volkov et al. (Chuvash State University, Cheboksary, USSR 1986) pp. 94-96.

Barker et al., "Vacuum Pack Technique of Temporary Abdominal Closure"; J. of Traumatic Injury, Infection, and Critical Care, vol. 48, No. 2 (2000).

Bevan, D. et al., "Diverse and potent activities of HGF/SF in skin wound repair", Journal of Pathology, vol. 203, 2004, pp. 831-838, in 8 pages.

Blumberg, J. et al., The Effect of Specific Compression on Soft-Tissue Response to Formalinized PVA (Ivalon) Sponge: A Critical Evaluation, Annals Surg., Mar. 1960, vol. 151(3), pp. 409-418, in 10 pages.

Boland, E.D. et al. "Utilizing acid pre-treatment and electrospinning to improve biocompatibility poly(glycolic acid) for tissue engineering", J. Biomed. Mater. Res. Part B: Appl Biomater 71B 144-152, 2004, in 9 pages.

Boland, E.D. et al., "Tailoring Tissue Engineering Scaffolds Using Electrostatic Processing Techniques: A Study of Poly(Glycolic Acid) Electrospinning", Journal of Macromolecular Science A. Pure and Applied Chemistry, A38(12), pp. 1231-1243 (2001), in 13 pages.

Brock, W.B. et al., "Temporary closure of open abdominal wounds: the vacuum pack", The American Surgeon, Jan. 1995, vol. 61(1), pp. 30-35, abstract, in 6 pages.

Declaration of Nadeem Bridi submitted in the Opposition against EP 2 395 957, dated Jan. 25, 2017, in 1 page.

Fleischmann, W. et al. "Vacuum Sealing for Treatment of Soft Tissue Injury in Open Fractures," Emergency Surgery (1993), vol. 96, pp. 488-492, in 5 pages.

Garner, G. et al., "Vacuum-assisted wound closure provides early fascial reapproximation in trauma patients with open abdomens," Am. J. of Surgery, vol. 182 (2001), pp. 630-638, in 9 pages.

Harris, D., "A new technique of skin grafting using Stei-Greffe and a self-adhering foam pad," Brit. J. of Plastic Surg., vol. 34, No. 2, Apr. 1981, pp. 181-185, in 6 pages.

Hougaard, H. et al., "The open abdomen: temporary closure with a modified negative pressure therapy technique," International Wound Journal, 2014, pp. 13-16, ISSN 1742-4801, in 4 pages.

International Search Report, re PCT Application No. PCT/GB2010/000228, dated May 12, 2010.

International Preliminary Reporton Patentability, re PCT Application No. PCT/GB2010/000228, dated Aug. 25, 2011.

Jeter, K. et al., "Managing Draining Wounds and Fistulae: New and Established Methods", Chronic Wound Care, 1990, pp. 240-246, in 7 pages.

KCI Licensing, "V.A.C. Abdominal Dressing System Advanced Management of the Open Abdomen," 2004, in 6 pages.

KCI USA, Inc., "V.A.C. Therapy Safety Information", leaflet, 2008.

KCI V.A.C. Simplace Dressing Brochure 2008, in 2 pages.

Ma, P., "Scaffolds for tissue fabrication", Materials Today, Review, May 2004, in 11 pages.

Middleton, J. et al., "Synthetic biodegradable polymers as medical devices" (HTML), Medical Plastics and Biomaterials Magazine, Mar. 1998, in 14 pages.

Mitchell, R. et al., "Role of Stem Cells in Tissue Homeostasis", Pocket Companion to Robbins and Cotran Pathologic Basis of Disease, 7th Edition, 2006, in 3 pages.

Navsaria, P.H. et al., "Temporary closure of open abdominal wounds by the modified sandwich-vacuum pack technique", British Journal of Surgery, 2003, vol. 90, pp. 718-722, in 8 pages.

Nicholas, J.M., "Options for Management of the Open Abdomen", Presentation from Emory University School of Medicine, Invited Speaker American College of Surgeons 32nd Annual Spring Meeting, General Session 12—Presentation and Panel Discussion on the Open Abdomen in General Surgery—How Do You Close the Abdomen When You Can't—Boston Marriott Copley Place Hotel, Boston, MA Apr. 26, 2004, in 66 pages.

Notice of Opposition—Statement of Facts and Evidence, re European Patent No. EP 2 395 957, dated Jan. 27, 2017, in 11 pages.

Orgill, D.P. et al., "Guidelines for Treatment of Complex Chest Wounds with Negative Pressure Wound Therapy", Wounds, a Compendium of Clinical Research and Practice, Suppl. B, Dec. 2004, pp. 1-23, in 26 pages.

Schein, M. et al., "The 'Sandwich Technique' in the Management of the Open Abdomen," British Journal of Surgery, 1986, vol. 73, May 1986, pp. 369-370, in 2 pages.

Smith, L. et al., "Vacuum Pack Technique of Temporary Abdominal Closure: A Four-Year Experience", The American Surgeon, Dec. 1997, pp. 1102-1108; vol. 63, No. 12.

Solovev, V.A., "Treatment and Prevention of Suture Failures after Gastric Resection" (Dissertation Abstract) (S.M. Kirov Gorky State Medical Institute, Gorky USSR 1988).

Stewart, J., "World Wide Wounds—Next Generation of Products for Wound Management", 2002, in 13 pages.

Forwarding a Letter of Opponent in Reply to the Proprietor Letter for European Patent No. 2395957, dated Jun. 26, 2020, 3 pages.

Annex to the Communication, re the Opposition of European Patent No. EP2395957, mailed on Oct. 27, 2017, 11 pages.

(56) References Cited

OTHER PUBLICATIONS

Brief Communication—Letter from the Opponent, re the Opposition of European Patent No. EP2395957, mailed on Mar. 28, 2018, 9 pages.
Brief Communication—Letter from the Proprietor of the Patent, re the Opposition of European Patent No. EP2395957, mailed on Apr. 23, 2018, 29 pages.
Grounds for the Decision and Annex to Communication, re the Opposition of European Patent No. EP2395957, mailed on Jul. 6, 2018, 56 pages.
Information about the Result of Oral Proceedings, re the Opposition of European Patent No. EP2395957, mailed on Jun. 15, 2018, 9 pages.
Letter relating to the Appeal Procedure, re the Opposition of European Patent No. EP2395957, mailed on May 1, 2019, 6 pages.
Letter Relating to the Appeal Procedure, re the Opposition of European Patent No. EP2395957, mailed on Dec. 24, 2019, 41 pages.
Notice of Appeal, re the Opposition of European Patent No. EP2395957, mailed on Sep. 6, 2018, 6 pages.
Reply of the Patent Proprietor to the Notice(s) of Opposition, re the Opposition of European Patent No. EP2395957, mailed on Jul. 10, 2017, 3 pages.
Reply to Appeal, re the Opposition of European Patent No. EP2395957, mailed on Mar. 18, 2019, 42 pages.
Statement of Grounds of Appeal, re the Opposition of European Patent No. EP2395957, mailed on Nov. 6, 2018, 34 pages.

* cited by examiner

The blade length (end to end of each cross) is 18 mm

WOUND PACKING

CROSS-REFERENCE TO RELATED APPLICATIONS

This application is a continuation of U.S. patent application Ser. No. 15/187,558, filed Jun. 20, 2016, entitled WOUND PACKING, which is a continuation of U.S. patent application Ser. No. 14/328,323, filed Jul. 10, 2014, entitled WOUND PACKING, which is a continuation of U.S. patent application Ser. No. 13/201,427, filed Sep. 14, 2011, entitled WOUND PACKING, which is a U.S. National Phase of PCT International Application No. PCT/GB2010/000228, filed on Feb. 10, 2010, designating the U.S. and published on Aug. 19, 2010 as WO 2010/092334, which claims priority to Great Britain Patent Application No. 0902368.0, filed on Feb. 13, 2009. The disclosure of all of the prior applications are incorporated by reference herein in their entireties and should be considered a part of this application.

BACKGROUND OF THE DISCLOSURE

Field of the Invention

The present invention relates to a porous wound packing material and methods of its manufacture and use. In particular it relates to a wound packing material which is adapted to allow it to be easily shaped and configured to the shape of a wound. Such wound packing materials are particularly suitable for negative pressure wound therapy (NPWT).

Background

NPWT is a relatively new treatment for open wounds. Typically in NPWT the wound cavity or surface is filled or covered with a material that allows the transmission of a partial vacuum (i.e. does not completely collapse) to the wound bed when a negative pressure is applied to the wound area, and also allows fluids to pass from the wound bed towards the source of negative pressure. There are two primary approaches to NPWT, i.e. gauze or foam types. The gauze type (also referred to as the Chariker-Jeter technique) involves the use of a drain wrapped in gauze topped by a sealed dressing. The foam type involves the use of foam placed over or in the wound. The present invention is directed primarily towards the foam type of NPWT.

In foam based NPWT the wound cavity is filled or covered with a porous foam packing material and covered over and sealed with flexible sheet (a drape) that is fairly impermeable to fluids. A tube is inserted under or through the drape into the wound site and its distal end is connected to a vacuum source (commonly a pump). The wound cavity, enclosed by the drape and tissue, contracts under the force of atmospheric pressure and compresses the packing material visibly. Gross tissue movement ceases after a few tens of seconds and fluid flow from the wound (withdrawn from the tissue) ensues. The fluid is transmitted through the packing material and up the vacuum tube to a collection receptacle positioned between the distal end of the tube and the vacuum source. The wound packing material mechanically supports the tissue to which it is applied, and also allows the free flow of fluids away from the site when a vacuum is applied, even when compressed. A good material for this application is hydrophobic, reticulated polyurethane foam of very high free internal volume.

The packing material for use in NPWT must be shaped to fit the wound to be packed. This is typically achieved by the medical practitioner (typically physician or nurse) cutting a preformed block of foam (usually a cuboid) to approximately fit the wound using a scalpel, knife or scissors. This operation can be complex, time consuming and messy for the medical practitioner, and indeed can be dangerous with the possibility of particulate foam material contaminating the wound site or of an accident during the cutting process. Accordingly, the process of shaping the wound dressing is currently an unaddressed problem in the field of NPWT which is a barrier to its effective and widespread use.

SUMMARY OF SOME EXEMPLIFYING EMBODIMENTS

According to the present invention there is provided a wound packing material comprising a body of a porous material, the body comprising frangible regions defining a plurality of portions, the frangible regions allowing the portions to be selectively removed from the body.

The term frangible is intended to mean that the material has been weakened in some manner which allows the portion to be removed relatively easily (e.g. manually) from the body without substantially damaging the remainder of the body, but where the overall structure of the body is sufficiently strong that the body remains intact during normal use, i.e. in the absence of manipulation to remove a portion. It is highly preferred that the portions can be removed manually, without the use of additional tools such as scissors, knives, scalpels etc. This allows a medical practitioner to remove portions to achieve a desired shape of the body quickly and simply without the need to use additional tools.

Preferably the frangible regions are defined by partial pre-cuts formed in the body.

Use of the term partial pre-cuts is intended to mean a region of the body where the material of the body has been removed or severed to at least partially separate a portion of the body from the rest of the body, but where sufficient material of the body has been left such that the body retains its general structural integrity, i.e. sufficient integrity for general storage, handling and use as a wound packing material. However, the remaining material is sufficiently weak (i.e. frangible) that it is relatively easily severable with manually applied force, e.g. by a medical practitioner tearing the portion from the body.

It should be noted that the term partial pre-cuts is intended to cover both situation where material is removed by cutting or otherwise removing or severing regions of a preformed body of porous material, and also where the pre-cuts are formed during initial production of the body, e.g. formed during a moulding process.

Preferably the wound packing material is a wound packing foam suitable for use in negative pressure wound therapy (NPWT). Particularly suitable foams for NPWT include polyurethane foam, typically reticulated polyurethane foam of very high free internal volume, e.g. 80% or higher, preferably 90% or higher free internal volume. Typical foams used in NPWT have porosities in the range 30-60 ppi (pores per inch) and pore diameters in the range 300-800 μm. However, other suitable foams are known in the art and may be equally suitable. In general suitable foams have an open porous structure, to allow transmission of the negative pressure to the wound bed, and sufficient mechanical strength to prevent the negative pressure (typically approximately 80-125 mm Hg below ambient atmospheric pressure) from substantially collapsing the structure of the foam.

It is highly preferred that the wound packing material is sterile. This can be achieved using conventional sterilisation techniques which are known for sterilising surgical foams and dressings.

It will be clear to the person skilled in the art that size and shape of the selectively removable portions will be determined by the number of frangible regions provided per unit volume of the body, and the number of different orientations and configurations that the frangible regions are provided in.

As mentioned above, the frangible regions are preferably defined by partial pre-cuts within the body—the following description will focus on embodiments whereby the frangible regions are formed in this way, but it will be understood that frangible regions could be formed in other manners (e.g. selectively weakening the foam structure at selected regions using chemically agents or heat) and that such variants are within the scope of the present invention.

It is preferred that the partial pre-cuts are generally planar. In particular, flat planar partial pre-cuts are preferred as they provide for regularly shaped portions. However, it is perfectly possible that the planes could be curved where a curved profile on an exposed region of the body following removal of the portions is preferred.

Suitably the body comprises a first set of substantially parallel planar partial pre-cuts in first orientation. The set may comprise a plurality of planar pre-cuts, each planar pre-cut comprising a series of individual pre-cuts, each individual pre-cut being spaced from the adjacent pre-cut by a gap. The individual pre-cuts are aligned with the plane defined by the planar parallel partial pre-cut. Preferably the parallel planar partial pre-cuts of the set are regularly spaced. Where one set of parallel planar partial pre-cuts is provided in a single orientation it will be apparent that the removable portions defined by the set of planar partial pre-cuts will be slices of the body; each slice is removable from the next slice as a result of the planar parallel partial pre-cut between them.

It is preferred that the spacing between each of the parallel planar pre-cuts in the set is 30 mm or less, preferably 25 mm or less, especially 20 mm or less, and optionally 15 mm or less. The size of the portions are defined by the spacing between the parallel planar pre-cuts in the set—in this case the slices would have a thickness corresponding to the spacing between each plane.

The partial pre-cuts sever a substantial amount of the material in the plane being cut, leaving one or more relatively narrow pieces of material attaching the portion to the body (i.e. a gap), the relatively narrow piece of material thus forming the frangible region. It is desirable that the partial pre-cuts define a repeating pattern of severed regions with intervening frangible regions, i.e. perforation. It is preferred that the severed regions have a width of from 10 mm to 30 mm, preferably from 15 mm to 25 mm, and optionally from 16 to 22 mm, especially around 18 mm, and that the remaining frangible regions have a width of from 1 mm to 5 mm, preferably 1 to 3 mm, especially around 2 mm.

In another way of considering the spacing and size of the individual partial pre-cuts, typically the ratio of length of severed material to remaining material will be around 3 to 1 or higher (e.g. 15 mm severed and 5 mm remaining, or a ratio equivalent thereof), preferably 6 to 1 or higher (e.g. 18 mm severed and 3 mm remaining, or a ratio equivalent thereof), especially 9 to 1 or higher (e.g. 18 mm severed and 2 mm remaining, or a ratio equivalent thereof).

In a particularly preferred embodiment the pre-cut severs from 15 to 19 mm and leaves a frangible region of from 1 to 5 mm, preferably 17 to 19 mm and leaves a frangible region of from 1 to 3 mm, and especially approximately 18 mm leaving a frangible region of approximately 2 mm width.

Conveniently such a cut can be made using a die cutting apparatus comprising an array of a set of parallel planar blades, the set comprising a plurality of series of blades arranged in a plane, each blade having a width corresponding to the width of the region to be severed, and a spacing between the adjacent blades within a series corresponding to the width of the frangible region. The spacing between each planar series of blades defines the thickness of the frangible portion.

Thus in a preferred embodiment of the invention, the wound packing material comprises partial pre-cuts formed by die-cutting. Alternative methods of forming the partial pre-cuts such as laser cutting or high pressure fluid cutting might be used as alternatives to die-cutting.

It is preferred that the body comprises a second set of parallel planar partial pre-cuts in a second orientation. Again, it is preferred that the partial pre-cuts are regularly spaced, and the dimensions set out above in relation to the first set of partial parallel planar pre-cuts are equally applicable to the second set.

The second set of partial pre-cuts may also be made by die cutting.

The second set may suitably provided at a second orientation which is substantially perpendicular to the first orientation, i.e. where the first second sets of pre-cuts intersect, it will be substantially at a right angle. The pre-cuts of the first and second sets could thus be said to lie on nominal X and Y planes respectively.

It will be apparent that where two sets of pre-cuts are provided, the selectively removable portions will typically be smaller than where one set of partial pre-cuts is provided, i.e. the second set will sub-divide the portions formed by the first set. Thus it could be said that the body has a higher volumetric resolution in that it is split into finer units.

Generally the shape of portion provided when a first and second set of partial pre-cuts is used will be substantially a cuboid, the width and breadth of which is defined by the spacing of the planes in each of the partial pre-cuts, the length being defined by the relative dimension of the body in a nominal Z plane. This applies for flat planar pre-cuts; where non-flat planar cuts are provided, such regular shapes will not be provided.

It is preferred that the body comprises a third set of parallel planar partial pre-cuts in a third orientation. Again, it is preferred that the pre-cuts are regularly spaced, and the dimensions set out above in relation to the first and second sets of partial pre-cuts are equally applicable to the third set.

The third set may suitably be provided at a third orientation which is substantially perpendicular to both the first and second set of pre-cuts. Thus it could be said that the third set of pre-cuts lies on the Z plane, relative to the X and Y planes of the first and second sets respectively. Where three such sets are provided, the resultant selectively removable portions will be generally cuboids. Where the spacing between the planar partial pre-cuts are the same in each of the three sets, the resultant selectively removable portions will be substantially cubic.

It is of course possible to provide more than three sets of partial pre-cuts, and vary the angles between the pre-cuts to increase resolution and provide for a greater control over the shape and size of the selectively removable portions. However, where more than three sets are provided, the engineering difficulties in terms of physically forming the pre-cuts and also in retaining the general structural integrity of the body become considerable. In fact, even providing three sets of cuts in the X, Y and Z planes (i.e. a 3D pre-cut body) is somewhat difficult to achieve, and it is a significant aspect of the present invention that this has made possible.

As mentioned above, the spacing of the parallel planar partial pre-cuts, in particular the spacing between each pre-cut plane, dictates the size and shape of the selectively removable portions. A spacing of 20 mm, for example, in all 3 sets of a 3D pre-cut body provides for portions which are cubes of approximately 20 mm in each dimension. This allows a medical practitioner to remove cube shaped portions of foam to shape the body to the desired shape for wound packing, and to achieve a fit to the shape of the wound to within 20 mm. Alternatively, blocks of 20×20×10 mm may be a suitable shape allowing increased resolution one dimension, but retaining a relatively manageable number of portions. It is, of course, generally desirable to allow the medical practitioner to shape the body of wound packing material as closely as possible to the desired shape for wound packing, but this must be balanced against the need for ease of manufacture and simplicity of handling. It has been found that such a balance can be achieved using dimensions of from 10 to 20 mm for the removable portions.

It should be pointed out that in certain instances it may be sufficient to have the ability to remove portions to achieve a far less precise shape of body of wound packing material. In such situations a body comprising three sets of pre-cuts may not be required, and a body comprising one or two sets of parallel planar partial pre-cuts may provide sufficient scope for customisation of shape.

However, it is an objective of the present invention to provide a wound packing material which is highly customisable, and that a body comprising three or more sets of parallel planar partial pre-cuts is generally preferred.

Accordingly, in a particularly preferred embodiment the present invention provides a wound packing material comprising a body of a porous material, the body comprising frangible regions defining a plurality of selectively removable cuboidal portions, the frangible regions being defined by partial pre-cuts provided in the body of the body.

Preferably the body is entirely comprised of selectively removable cuboidal portions interconnected by frangible regions, each of the edges of the cuboids being 5 to 30 mm, preferably from 10 to 24 mm, especially from 10 to 20 mm.

More preferably the cuboidal portions are cubic and have an edge length of from 5 to 30 mm, preferably from 10 to 24 mm, especially from 10 to 20 mm.

Suitably the body is generally cuboidal in shape, prior to the removal of any selectively removable portions. The body may suitably be a cube, or it may be a rectangular cuboid or square cuboid. Various shapes of body may be useful for different wound shapes and sizes. Typically NPWT foam is provided as a rectangular cuboid of approximate dimensions 200×100×30 mm, and this is a suitable shape for the body of the present invention. For such a shape and size, portions of approximately 20×20×10 mm are very suitable to allow customisation of shape.

In a further aspect the present invention provides a method of manufacture of a wound packing material, the method comprising the steps of:
providing a body of a porous wound packing material;
forming at least one partial pre-cut in a first orientation in said body, said at least one partial pre-cut severing regions of the body to leave frangible regions of the body, the frangible regions allowing the portions to be selectively removed from the body.

Preferably the at least one partial pre-cut is a parallel planar partial pre-cut.

Preferably the at least one partial pre-cut is formed by die cutting.

The die cutting may involve providing at least one blade and pushing said blade through the body to cut a region of the body and leave at least one frangible region.

It is preferred that the die cutting involves providing a plurality of blades in a suitable arrangement to provide desired partial pre-cuts and frangible regions. Dimensions and other details of the partial pre-cuts are set out above.

Suitably the blades have a length great enough to pass completely through the body. It should be noted that the body may be compressed as it is cut, and therefore the blades need only be long enough to pass completely through the body as it is compressed in the cutting process. Alternatively the blades may be shorter where it is not desirable to cut all the way through the body, or where cuts from two sides will be made to cut completely through the body; in the latter case the blades will generally have a length of approximately half of the relevant dimension of the compressed body to be cut.

The blades may suitably be arranged as an array of a set of parallel planar flat blades, the set comprising a plurality of series of individual flat blades arranged in a plane, each individual flat blade having a width corresponding to the width of the region to be severed, and a gap between the individual flat blades corresponding to the width of the frangible region. Suitable details of the blades are set out above.

Suitably the method involves the step of forming a second partial pre-cut in a second orientation, especially a second set of partial pre-cuts as discussed above. Preferably the second orientation is perpendicular to the first orientation. Preferably the second partial pre-cut is a parallel planar partial pre-cut.

Suitably the method involves the step of forming a third partial pre-cut in a third orientation, especially a third set of partial pre-cuts as discussed above. Preferably the third orientation is perpendicular to the first and second orientations. Preferably the third partial pre-cut is a parallel partial planar pre-cut.

Thus the method may involve providing three partial pre-cuts in nominal X, Y and Z planes. Suitably the X, Y and Z planes are congruent with the faces of the body, where the body is a cuboid.

Suitably the method involves forming partial pre-cuts to define a plurality of regularly shaped and sized cuboidal portions interconnected by frangible regions. Suitably the entire body is formed of selectively removable cuboidal portions. Suitably the cuboidal portions are cubes.

In certain embodiments two or more sets of pre-cuts can be made simultaneously. This can be suitably carried out using a single array of blades comprising two sets of blades in two orientations, e.g. an array of cruciform blades.

Where there is a risk of excessive distortion to the body during the cutting process it is useful to support the foam structure during the cutting process.

In a further aspect of the present invention there is provided a method of preparing a wound packing material comprising the steps of:
providing a wound packing material as set out above; and
removing portions of the body of said would packing material such that the body is a desirable shape.

Preferably the body is shaped to approximately fit the shape of a wound to be packed.

Preferably the portions are removed manually, i.e. without the use of tools.

In a further aspect the present invention provides a method of treating a wound comprising the steps of;
   providing a wound packing material as set out above;
   removing portions of the body of said would packing material such that the body is a desirable shape to fit within said wound; and
   packing the wound with said wound packing material.

Preferably the method provides the step of applying a negative pressure to the wound through the wound packing material, i.e. the method is NPWT. In general this can be achieved by providing a substantially fluid impermeable sheet over the wound and wound dressing, thus defining a sealed volume, and applying a negative pressure inside said sealed volume. The seal need not be completely hermetic, but should be sufficient to allow a suitable negative pressure to be sustained. The source of negative pressure, e.g. a pipe form a vacuum pump, is provided at a position such that it draws fluids from the wound bed through the wound packing material.

Suitably the negative pressure is in the range of from 80 to 125 mm Hg below ambient atmospheric pressure.

In a further aspect the present invention provides the use of a wound packing material as set out above in wound treatment, especially NPWT.

BRIEF DESCRIPTION OF THE DRAWINGS

Embodiments of the present invention will now be described, by way of example only, with reference to the accompanying drawings, in which.

DETAILED DESCRIPTION OF SOME EXEMPLIFYING EMBODIMENTS

Figure 1:
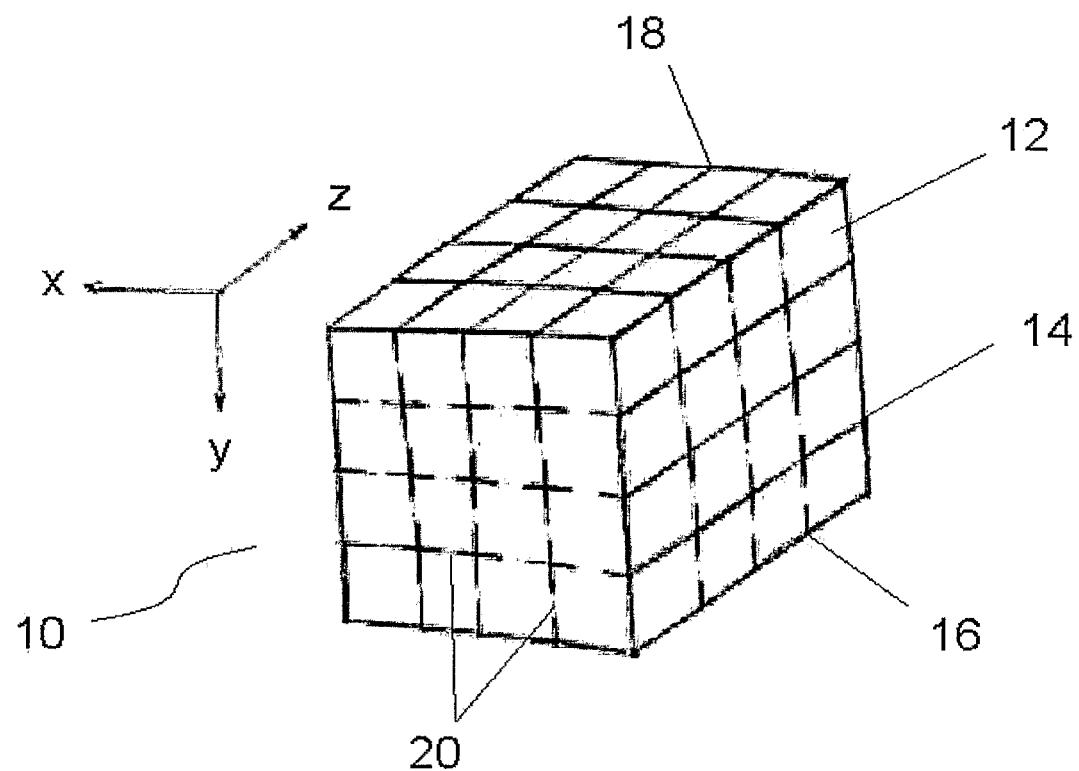
FIG. 1 shows a body of porous wound packing material after being pre-cut in the x, y and z dimensions.

As shown in FIG. 1, a body 10 of porous material, such as foam, is generally a cube in shape having three dimensions, x, y and z. The porous material is suitable for wound packing. The material may be reticulated polyurethane foam of very high free internal volume. The body 10 could be a different shape, e.g. a comparatively flat cuboid, which is a conventional shape for foams for NPWT.

Figure 2:
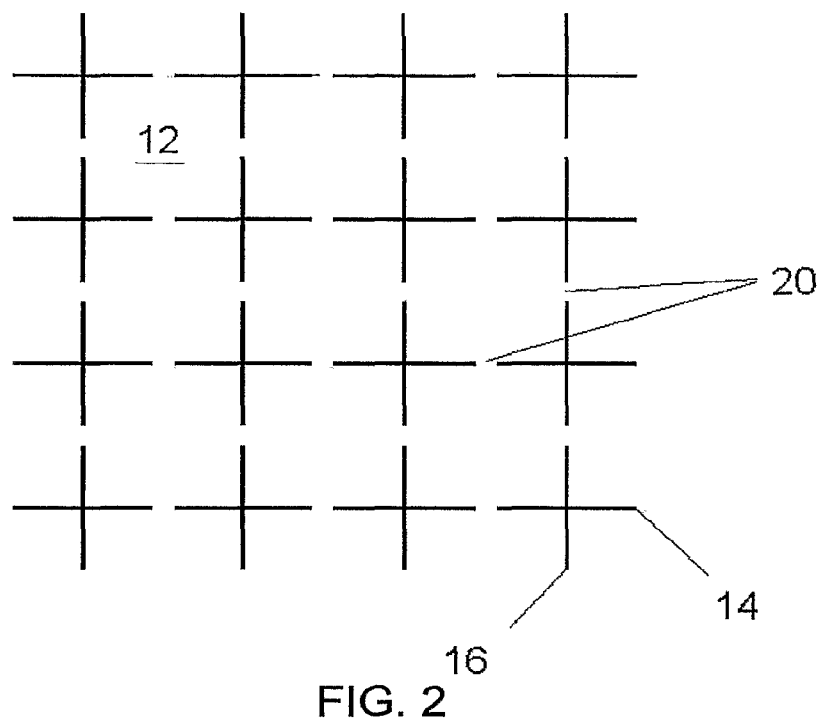
FIG. 2 schematically shows the set of pre-cuts in the x and y dimension.
Figure 3:
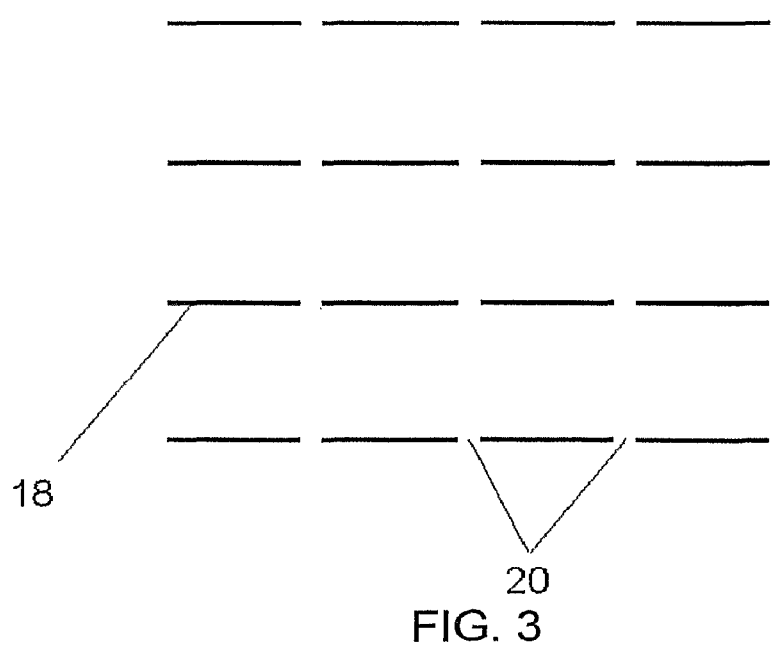
FIG. 3 schematically shows the sets of pre-cuts in the z dimension.

As shown in FIG. 2, the body 10 is partially pre-cut by a suitable cutting technique, such as die cutting (though other techniques may be useable), in the planes in the x and y dimensions to define a first and second set of parallel planar partial pre-cuts 14, 16. The body 10 is also partially pre-cut in the z dimension to define a third set of parallel planar partial pre-cut 18. The three sets of partial pre-cuts 14, 16, 18 define individual cubic portions 12 of approximately equal volume.

The three sets of partial pre-cuts 14, 16, 18 are intermittent, the gaps in the pre-cuts defining frangible regions 20 on each internal face of each portion 12 (in other words they are perforated for easy removal of the portions). The frangible regions 20 connect adjacent portions 12 together thereby to ensure the portions 12 remain connected together when the body 10 is stored, compressed or extended, i.e. when being used as a wound packing in NPWT.

The frangible regions 20 extend between face sides of each portion 12 and are elongate. The thickness of each frangible region 20 is suitable to provide adequate strength to ensure adjacent portions 12 remain connected when the body 10 is being compressed or extended during normal use, whilst allowing one or more portions 12 to be easily pulled from the body 10 by compromising the integrity of the frangible regions 20 attaching the portion 12 to the body. For typical NPWT foams, a frangible region of approximately 2 mm of thickness provides a good compromise of strength versus tearability.

One or more portions 12 can be selectively removed by hand from the body 10 to shape the body 10 for a particular wound packing application. Advantageously, cutting tools such as knives, scalpels and scissors are not required to shape the body 10 of porous material.

Figure 4:
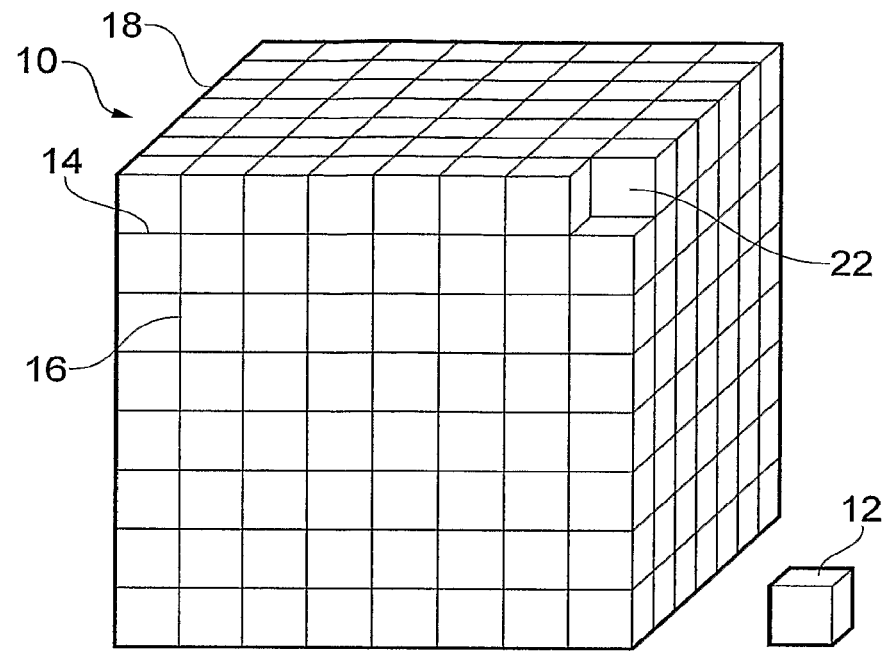
FIG. 4 shows a body with a single portion removed.
Figure 5:
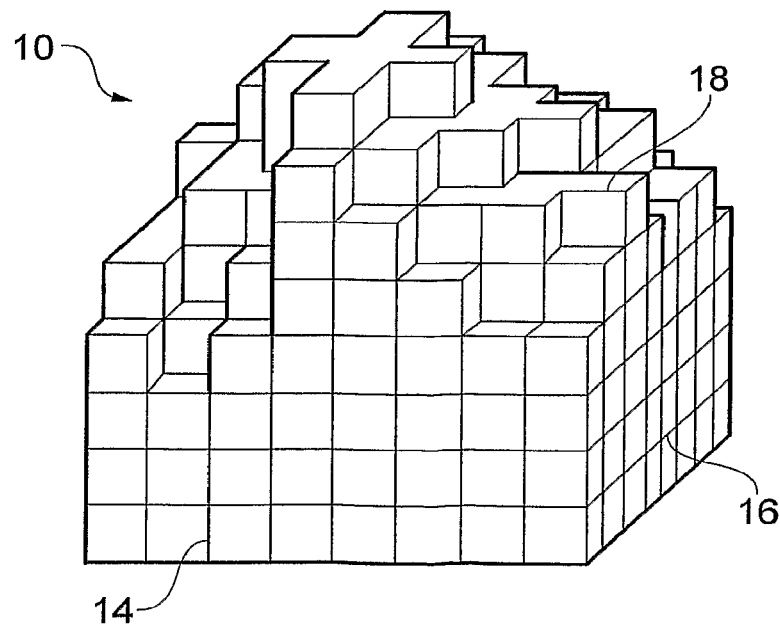
FIG. 5 shows the body of FIG. 4 with a plurality of portions removed.

As shown in FIGS. 4 and 5, the body 10 is a cube of volume 448000 mm$^3$, which is pre-cut in the x, y and z dimensions to define 448 (i.e. 7×8×8) equally sized 1000 mm$^3$ portions 12 (i.e. 10×10×10 mm). Adjacent portions 12 are connected by a frangible portion 20 of 2 mm thick porous material (not shown).

The frangible regions 20 ensure the body 10 retains its structural integrity for storage and handling purposes whilst allowing one or more portions 12 to be selectively removed therefrom. FIG. 4 shows a single portion 12 removed from the body 10 to leave a hole 22, whilst FIG. 5 shows a plurality of portions 12 removed from the body 10 to selectively shape the body 10 for a particular application of wound packing. The body 10 may be shaped to complement the external contours of a patient or to fit in a cavity.

Of course, the dimensions of the body 10 and the portions 12 may be different to those described above for a particular application and the number and orientation of partial pre-cuts lines 14, 16, 18 may be varied and may be planar or curved to define regular or irregular portions 12 accordingly.

To form a wound packing material similar to the above the following general process may be used. The present process describes a process for converting a single cuboid block of foam into 6 cuboidal wound packing material bodies. The block is initially approximately 200 mm by 100 mm by 180 mm and is cut into 6 blocks of 200 mm by 100 mm by 30 mm. It will be apparent that variations of this method could be used to manufacture wound packing materials of a great variety of different shapes and sizes, and having varying portion size and shapes.

Figure 6:
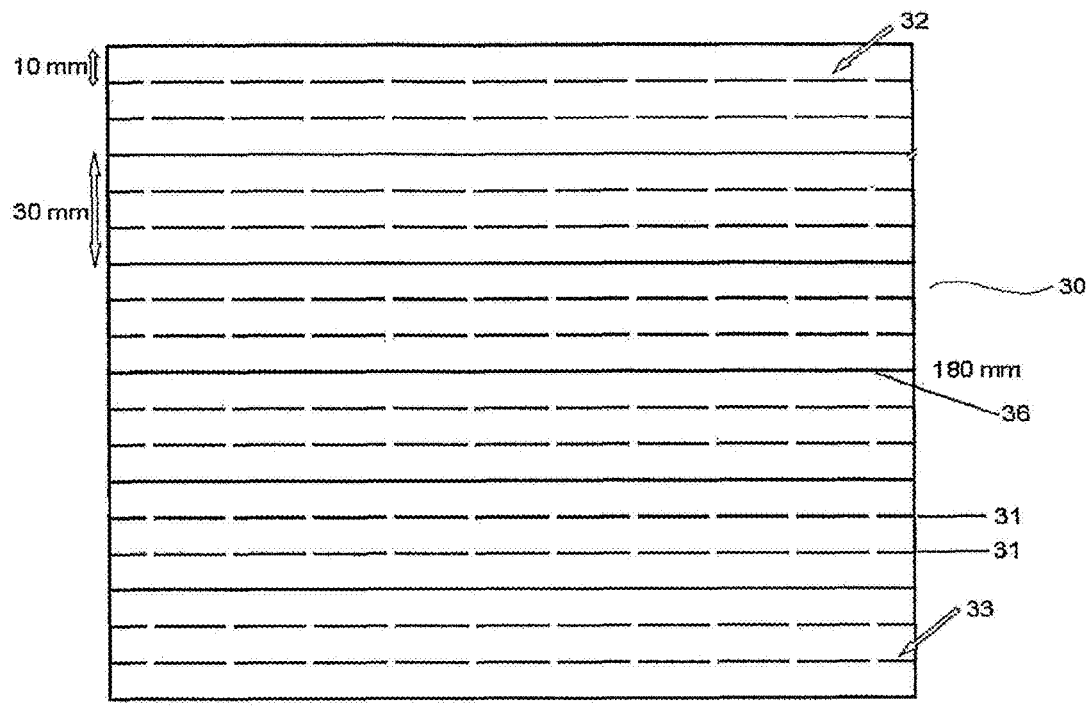
FIG. 6 shows a first array of a set of blades suitable for forming a partial pre-cut in a first orientation in a body of wound packing material.

A body of porous material is provided which has the dimensions set out above.
   A first set of parallel planar partial pre-cuts is made in the body using an array of blades 30. The pre-cuts are made perpendicular to, and into, a first face of the body
   The array (FIG. 6) comprises a number of planes 31 made up of a series of 18 mm wide flat blades 32, and a 9 mm blade 33 at each end of the plane; a gap of 2 mm is provided between each blade in the series. A gap of 10 mm is left between each plane of blades. The array also comprises 5 continuous 100 mm long planar blades 36 which acts to cut the initial block completely into 6 smaller blocks.

The first set of partial pre-cuts is achieved by placing the block of foam against the array of blades 30 and urging the blades into and through the block. The pressure required may be generated by a hydraulic press (also known as a clicker press). This is a conventional form of die cutting and the necessary apparatus and techniques are well known to one skilled in the art.

Figure 7:
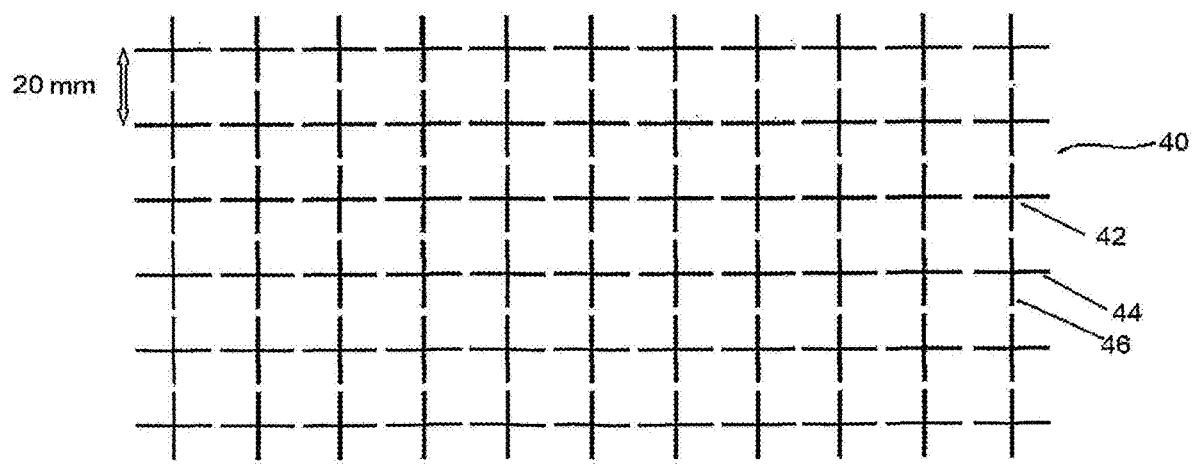
FIG. 7 shows a second array of sets of blades suitable for making second and third sets of partial pre-cuts in a body of wound packing material in second and third orientations.

Second and third sets of partial pre-cuts are made using a second array 40 of blades (see FIG. 7). In the second array a plurality of cruciform blades 42 are provided. Due to the shape and arrangement of the blades 42, the array is suitable to make two sets of parallel planar partial pre-cuts in two orientations, which are perpendicular to each other. Thus, in one cutting action, two sets of parallel planar partial pre-cuts are made. Each cruciform blade 42 comprises two 18 mm long linear blade elements 44,46 intercepting at each of their midpoints at a right angle to define the cruciform blade.

The cruciform blades are arranged in the array to form a square matrix with gaps of 2 mm provided between each cruciform blade.

As with the first cut, the second cut is made by applying pressure to drive the blades 42 through the body.

The length of the blades in the first and second array are sufficient to pass completely through the body and emerge at the other side.

This process forms 6 cuboids of foam measuring 200 mm×100 mm×30 mm, which are each formed of cuboids measuring approximately 20 mm×20 mm×10 mm, each of the cuboid portions being interconnected with adjacent portions by frangible regions of approximately 2 mm thickness.

It should be noted that where a generally cubic body of foam is being prepared the order of the cuts is not particularly significant as the cube is equally structurally stable in all 3 dimensions. However, when preparing a body with a relatively thin minor dimension, as set out in the method above, it is important that the first cut made is the one perpendicular to the plane of the thin dimension (i.e. the smallest face of the cuboid), or that the shape of the block is supported as the cut is made. If the order is reversed, or the block shape is not supported, there is generally an unacceptable amount of crushing and/or corrugation of the body resulting in a significant distortion to the desired cut geometry.

The result of this process is a wound packing material which can be custom shaped by manually removing cuboid portions by tearing the frangible regions interconnecting the portions making up the body. This allows a medical practitioner to shape the body of wound packing material to fit the wound to be packed or dressed. Once the wound packing material has been shaped appropriately, the wound can be dressed for NPWT.

What is claimed is:

1. A wound packing material comprising:
a body of porous material, the body comprising a plurality of outer surfaces and a plurality of outer edges, each of the plurality of outer edges disposed at an interface of a pair of adjacent outer surfaces, each of the outer surfaces delimited by a subset of the plurality of outer edges, the body comprising frangible regions defining a plurality of portions, the frangible regions allowing the portions to be selectively removed from the body, wherein the wound packing material comprises a first partial pre-cut that extends in a first direction from a first outer surface of the body to a second outer surface of the body, wherein the wound packing material comprises a second partial pre-cut that extends in the first direction from the first outer surface of the body to the second outer surface of the body, wherein each of the first and second partial pre-cuts is spaced apart from each outer edge of the subset of outer edges that delimits the first outer surface, and wherein the wound packing material comprises a third partial pre-cut that extends in a second direction from a third outer surface of the body to a fourth outer surface of the body, wherein the third partial pre-cut is spaced apart from each outer edge of the subset of outer edges that delimits the third outer surface.

2. The wound packing material of claim 1, wherein the plurality of portions can be removed manually.

3. The wound packing material of claim 1, wherein the wound packing material is formed from a wound packing foam suitable for use in negative pressure wound therapy.

4. The wound packing material of claim 1, wherein the wound packing material does not substantially collapse when a negative pressure is applied to the wound packing material.

5. The wound packing material of claim 4, wherein the negative pressure is in the range of from 80 to 125 mm Hg below ambient atmospheric pressure.

6. The wound packing material of claim 1, wherein the body further comprises an upper surface, a lower surface, and a thickness defined therebetween, the body comprising at least one first partial pre-cut disposed within the thickness, an upper portion of the thickness being disposed between the at least one first partial pre-cut and the upper surface, a lower portion of the thickness being disposed between the at least one first partial pre-cut and the lower surface.

7. The wound packing material of claim 6, wherein the at least one first partial pre-cut is substantially parallel with the upper surface or the lower surface.

8. The wound packing material of claim 7, wherein the body further comprises at least one second partial pre-cut that is substantially perpendicular to the upper surface.

9. The wound packing material of claim 8, wherein the at least one second partial pre-cut is curved.

10. The wound packing material of claim 9, wherein the at least one second partial pre-cut comprises two or more spaced apart curved planar cuts that are substantially parallel with one another.

11. The wound packing material of claim 10, wherein the at least one second partial pre-cut comprises an additional curved planar cut that is non-parallel with the two or more spaced apart curved planar cuts.

12. A wound packing material comprising:
a body of porous material, the body comprising a plurality of outer surfaces and a plurality of outer edges, each of the plurality of outer edges disposed at an interface of a pair of adjacent outer surfaces, each of the outer surfaces delimited by a subset of the plurality of outer edges, the body comprising frangible regions defining a plurality of portions, the frangible regions allowing the portions to be selectively removed from the body, wherein the wound packing material comprises a first plurality of partial pre-cuts that extend in a first direction from a first outer surface of the body to a second outer surface of the body, wherein the wound packing material comprises a second plurality of partial pre-cuts that extend in the first direction from the first outer surface of the body to the second outer surface of the body, wherein each of the first plurality of partial precuts and each of second plurality of partial pre-cuts is spaced apart from each outer edge of the subset of outer edges that delimits the first outer surface, and wherein the wound packing material comprises a third plurality of partial pre-cuts that extend in a second direction from a third outer surface of the body to a fourth outer surface of the body, wherein each of the third and fourth outer surfaces is different from the first and second outer surfaces.

13. The wound packing material of claim 12, wherein the plurality of portions can be removed manually.

14. The wound packing material of claim 12, wherein the wound packing material is formed from a wound packing foam suitable for use in negative pressure wound therapy.

15. The wound packing material of claim 12, wherein the wound packing material does not substantially collapse when a negative pressure is applied to the wound packing material.

16. The wound packing material of claim 15, wherein the negative pressure is in the range of from 80 to 125 mm Hg below ambient atmospheric pressure.

17. The wound packing material of claim 12, wherein the body further comprises an upper surface, a lower surface, and a thickness defined therebetween, the body comprising at least one first partial pre-cut disposed within the thickness, an upper portion of the thickness being disposed between the at least one first partial pre-cut and the upper surface, a lower portion of the thickness being disposed between the at least one first partial pre-cut and the lower surface.

* * * * *

UNITED STATES PATENT AND TRADEMARK OFFICE
CERTIFICATE OF CORRECTION

PATENT NO. : 11,357,903 B2
APPLICATION NO. : 16/524484
DATED : June 14, 2022
INVENTOR(S) : Bryan Greener It is certified that error appears in the above-identified patent and that said Letters Patent is hereby corrected as shown below:

On the Title Page

Page 3, Column 1 item (56) (U.S. Patent Documents), Line 44, delete "Radi" and insert -- Radl --.

Page 3, Column 1 item (56) (U.S. Patent Documents), Line 51, delete "Radi" and insert -- Radl --.

Page 5, Column 2 item (56) (Other Publications), Line 25, delete "Reporton" and insert -- Report on --.

In the Specification

Column 7, Line 50, delete "orientations;" and insert -- orientations. --.

Column 8, Line 62, after "body" insert -- . --.

In the Claims

Column 11, Line 2, Claim 12, delete "precuts" and insert -- pre-cuts --.

Signed and Sealed this
Thirteenth Day of September, 2022

Katherine Kelly Vidal
*Director of the United States Patent and Trademark Office*